(12) United States Patent
Kozlowski et al.

(10) Patent No.: US 6,337,338 B1
(45) Date of Patent: Jan. 8, 2002

(54) HETEROARYL-ARYL UREAS AS IGF-1 RECEPTOR ANTAGONISTS

(75) Inventors: Michael R. Kozlowski; Robert T. Lum, both of Palo Alto; Steven R. Schow, Redwood Shores; Hugo O. Villar, Newark; Micheal M. Wick, Woodside, all of CA (US)

(73) Assignee: Telik, Inc., South San Francisco, CA (US)

( * ) Notice: Subject to any disclaimer, the term of this patent is extended or adjusted under 35 U.S.C. 154(b) by 0 days.

(21) Appl. No.: 09/464,360

(22) Filed: Dec. 15, 1999

Related U.S. Application Data

(60) Provisional application No. 60/112,513, filed on Dec. 15, 1998.

(51) Int. Cl.[7] .................. A61K 31/47; A61K 31/425
(52) U.S. Cl. .................. 514/311; 514/371; 514/372
(58) Field of Search .................. 514/371, 372, 514/311

(56) References Cited

U.S. PATENT DOCUMENTS

| 3,406,176 | A | * | 10/1968 | Kim et al. | .................. 546/162 |
| 6,040,321 | A | * | 3/2000 | Kim et al. | .................. 514/369 |

FOREIGN PATENT DOCUMENTS

| GB | 1 425 505 | 2/1976 |
| WO | 94/18170 | 8/1994 |
| WO | 96/40673 | 12/1996 |
| WO | 97/40028 | 10/1997 |
| WO | 97/49399 | 12/1997 |
| WO | 97/49400 | 12/1997 |
| WO | 99/00357 | 1/1999 |
| WO | 99/24416 | 5/1999 |
| WO | 99/65884 | 12/1999 |

OTHER PUBLICATIONS

Y. Sugiyama et al., "TMP–153, a novel ACAT inhibitor, inhibits cholesterol absorption and lowers plasma cholesterol in rats and hamsters", *Atherosclerosis*, 113(1), 71–78 (1995).

J.T. Stewart et al., "Synthesis and anti–neoplastic evaluation of some 9–substituted acridines", *J. Med. Chem.*, 13(4), 762 (1970).

\* cited by examiner

*Primary Examiner*—Alan L. Rotman
*Assistant Examiner*—Rita Desai
(74) *Attorney, Agent, or Firm*—Heller Ehrman White & McAuliffe LLP

(57) ABSTRACT

Methods for treating diseases associated with the activity of the insulin growth factor-1 receptor (IGF-1R), such as cancer, are provided. Methods for inhibiting cell growth and proliferation, especially of tumor cells, and promoting apoptosis are also provided. Each of these methods employs the use of a heteroaryl-aryl urea compound as an antagonist for IGF-1R.

22 Claims, 3 Drawing Sheets

HETEROARYL-ARYL UREAS AS IGF-1 RECEPTOR ANTAGONISTS

This application claims the benefit of U.S. Provisional Application No. 60/112,513 filed on Dec. 15, 1998.

BACKGROUND OF THE INVENTION a) Field of the Invention

The present invention relates to methods of treating disease with heteroaryl-aryl ureas which are antagonists of the insulin growth factor-1 receptor. In particular, the invention relates to methods of inhibiting tumor growth and methods of treating cancer.

b) Description of Related Art

A major feature of malignant cells is the loss of control over one or more cell cycle elements. These elements range from cell surface receptors to the regulators of transcription and translation (Hunter, *Cell*, 64:249–70(1991); Cantley et al., *Cell*, 64:281–302 (1991); Aaronson, *Science*, 254:1146–51 (1991); Hitwell et al., *Science* 266:1821–8 (1994); Baserga, *Cell*, 79:927–30 (1994)), including the insulin-like growth factors, insulin growth factor-1 (IGF-1) and insulin growth factor-2 (IGF-2). The insulin growth factor system consists of families of ligands, insulin growth factor binding proteins, and receptors. A major physiologic role of the IGI-1 system is the promotion of normal growth and regeneration (Lowe, in *Insulin-Like Growth Factors: Molecular and Cellular Aspects*, LeRoith, D., ed., Boca Raton: CRC Press, 1991:49; Mathews et al., *Endocrinology*, 123:2827–33 (1988); Lynch et al., *J. Clin. Invest.*, 84:640–6 (1989)). The cloning of the insulin growth factor-1 receptor (IGF-1R) (Ullrich et al., *EMBO J.*, 5:2503–12 (1986)) allowed for the definitive demonstration that the activation of an overexpressed IGF-1R can initiate mitogenesis (Pietrzkowski et al., *Cell Growth Diff.*, 3:199–205 (1992)) and promote ligand-dependent neoplastic transformation (Kaleko et al., *Mol. Cell Biol.* 10:464–73 (1990)). Furthermore, IGF-1R plays an important role in the establishment and maintenance of the malignant phenotype (*Insulin-Like Growth Factors: Molecular and Cellular Aspects*, LeRoith D, ed., Boca Raton: CRC Press, (1991); Masters et al., *Ann. NY Acad. Sci.*, 692: 89–101 (1993); Humbel, *Eur. J. Biochem.*, 190:445–62 (1990); Sara et al., *Physiol. Rev.* 70:591–614 (1990); Sussenbach, *Prog. Growth Factor Res.*, 1:33–40 (1989); Bondy et al., *Ann. Intern. Med.*, 120:593–602 (1994)).

IGF-1R is synthesized as a single polypeptide chain, which is then glycosylated and cleaved into separate alpha and beta subunits. The receptor exists as a heterodimer, with several disulfide bridges. The ligand-binding domain is located on the extracellular alpha subunit. Approximately one-third of the beta-subunit is extracellular and is connected to the intracellular portion by a single transmembrane domain. The tyrosine kinase catalytic site and the ATP binding site are located on the cytoplasmic portion of the beta-subunit.

Unlike the epidermal growth factor (EGF) receptor, no mutant oncogenic forms of the IGF-1R have been identified. However, several oncogenes have been demonstrated to affect IGF-1 and IGF-1R expression (Ullrich et al., *EMBO J.*, 5:2503–12 (1986)). It has been shown that cells with disrupted IGF-1R genes will not grow in serum-free medium supplemented with growth factors. In addition these cells cannot be transformed by transfection with SV40T antigen or ras, agents that efficiently transform corresponding wild-type cells (Sell et al., *Mol. Cell Biol.*, 14:3604–12 (1994); Sell et al., *Proc. Natl Acad. Sci. USA*, 90:11217–21 (1993)).

The correlation between a reduction of IGF-1R expression and resistance to transformation has been seen in several other systems as well. Prager et al. inhibited the growth and transformation of rat-I fibroblasts by introduction of a dominant negative mutant of the IGF-1R (Prager et al., *Proc. Natl. Acad. Sci. USA.*, 91:2181–5 (1994)). Others have used an antisense strategy to reduce production of IGF-1R. Exposure of cells to the mRNA antisense to IGF-1R RNA, prevents soft agar growth of several human tumor cell lines (Resnicoff et al., *Cancer Res.*, 55:2463–9 (1995); Resnicoff et al., *Lab. Invest.*, 69:756–60 (1993); Resnicoff et al., *Cancer Res.*, 54:4848–50 (1994); Shapiro et al., *J Clin. Invest.*, 94:1235–42 (1994)).

It is now established that a major mode of tumor survival is escape from apoptosis (Fisher, *Cell*, 78:539–42 (1994)). IGF-1R abrogates progression into apoptosis, both in vivo and in vitro (Kulik et al., *Mol. Cell. Bio.*, 17: 1595–1606 (1997); Lamm et al., *Cancer Res.*, 58:801(1998)). It has also been shown that a decrease in the level of IGF-1R below wild-type levels causes apoptosis of tumor cells in vivo (Resnicoff et al., *Cancer Res.*, 55:2463–2469 (1995); Resnicoff et al., *Cancer Res.*, 55:3739–3741 (1995)). The ability of IGF-1R disruption to cause apoptosis appears to be diminished in normal, non-tumorigenic cells (Barega, *Trends Biotechnol.*, 14:150–2 (1996)).

Hence, the ligand-activated IGF-1R appears to have at least three important functions. First, it is required for optimal growth, although some growth occurs even in its absence. Second, IGF-1R is also obligatory for the establishment and maintenance of the transformed phenotype and for tumorigenesis for several types of cells. It also appears to protect cells from apoptosis. These features make IGF-1R an attractive target for therapeutic interventions against abnormal growth.

To date, there are few reports of compounds that are selective IGF-1 receptor antagonists. Parrizas et al. describe tyrphostins that had some efficacy in vitro and in vivo (Parrizas et al., *Endocrinology*, 138:1427–33 (1997)). These compounds were of modest potency and selectivity over the insulin receptor.

Another family of compounds, heteroaryl-aryl ureas, are ubiquitous in the literature. They have a long history of biological applications. Recently, a number of heteroaryl-aryl ureas have been described as $5HT_{2c}$ receptor antagonists as treatments for CNS disorders (WO 94/18170; WO 95/01976; WO 94/22871; WO 94/04533; WO 94/14801; WO 93/18028). In addition, they have been reported as ligands for the benzodiazepine receptor (Shindo et al., *Heterocycles*, 1989, 29, 899), inhibitors to fat metabolism (DE 29284485), anti-inflammatories (EP 123146), pesticides (JP 04178362) and some derivatives as antimicrobials (Patel et al., *J. Inst. Chem.*(India), 1989, 61, 93). As such, several reports to the preparation of these compounds, both on solid phase and in solution have been reported (Buckman et al., *Tet. Lett.*, 1996, 37, 4439; Stewart et al., *J. Med. Chem.*, 1970, 13, 762)

SUMMARY OF THE INVENTION

The invention relates to the use of heteroaryl-aryl urea compounds which have been found to be antagonists of the IGF-1 receptor. These compounds, or salts thereof, are suitable for the treatment of essentially any mammalian disease condition in which the IGF-1 receptor plays an active role and where suppressing the activity of IGF-1R ameliorates the disease condition. The generic formula of the heteroaryl-aryl urea compounds useful in the present invention is as follows:

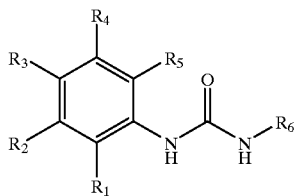

Formula I wherein $R_1$–$R_5$ are, independently, hydrogen, lower alkyl, substituted lower alkyl, hydroxyl, lower alkoxy, lower acyl, lower alkenyl, lower alkylthio, lower alkynyl, halo, $C(O)NR_7R_8$, $COOR_9$, $NR_{10}R_{11}$, a heterocyclic residue, aryl, aralkyl, cyano or nitro, any two adjacent substituents $R_1$–$R_5$ optionally together forming a lower alkylenedioxy, $R_6$ is a heterocyclic residue, $R_7$, $R_8$, $R_9$ are, independently, hydrogen, lower alkyl, substituted lower alkyl, aryl, aralkyl, or a heterocyclic residue, $R_{10}$, $R_{11}$ are, independently, hydrogen, lower alkyl, substituted lower alkyl, aryl, lower acyl, aralkyl, or a heterocyclic residue, and $R_7$ and $R_8$ or $R_{10}$ and $R_{11}$ together with the nitrogen may form a heterocyclic residue.

In one embodiment, $R_6$ is quinolinyl, optionally substituted.

One embodiment of the invention provides for a method of inhibiting the activity of the insulin-like growth factor-1 receptor in a mammalian cell. This method comprises administering an effective amount of a compound of formula I to the mammalian cell.

Another embodiment of the invention provides for a method of inhibiting the growth of a cell in a mammal. This method involves administering a compound of formula I to the cell in an amount sufficient to inhibit the growth of the cell.

Still another embodiment of the invention provides for a method of promoting apoptosis in a tumor cell, or more specifically, inhibiting the ability of a mammalian cell to escape from apoptosis. In this method, a compound of formula I is administered to the tumor cell in an amount sufficient to promote apoptosis.

The present invention also provides for a method of using a heteroaryl-aryl urea compound for the treatment of cancer. A method for treating cancer in a mammal is provided where a compound of formula I is administered to the mammal in a therapeutically effective, substantially non-toxic amount.

It is further contemplated by the present invention that the heteroaryl-aryl urea compounds of formula I may be used to inhibit an abnormal growth in a mammal. This method requires that a compound of formula I be administered to the abnormal growth of the mammal in a therapeutically effective, substantially non-toxic amount.

In a still further embodiment of the invention, a compound of formula I is used to treat an IGF-1R-related condition in a mammal by inhibiting the activity of IGF-1R in a tissue of the mammal his method comprises administering a compound of formula I to the tissue of the mammal in a therapeutically effective amount.

DETAILED DESCRIPTION OF THE INVENTION

Figure 1A:
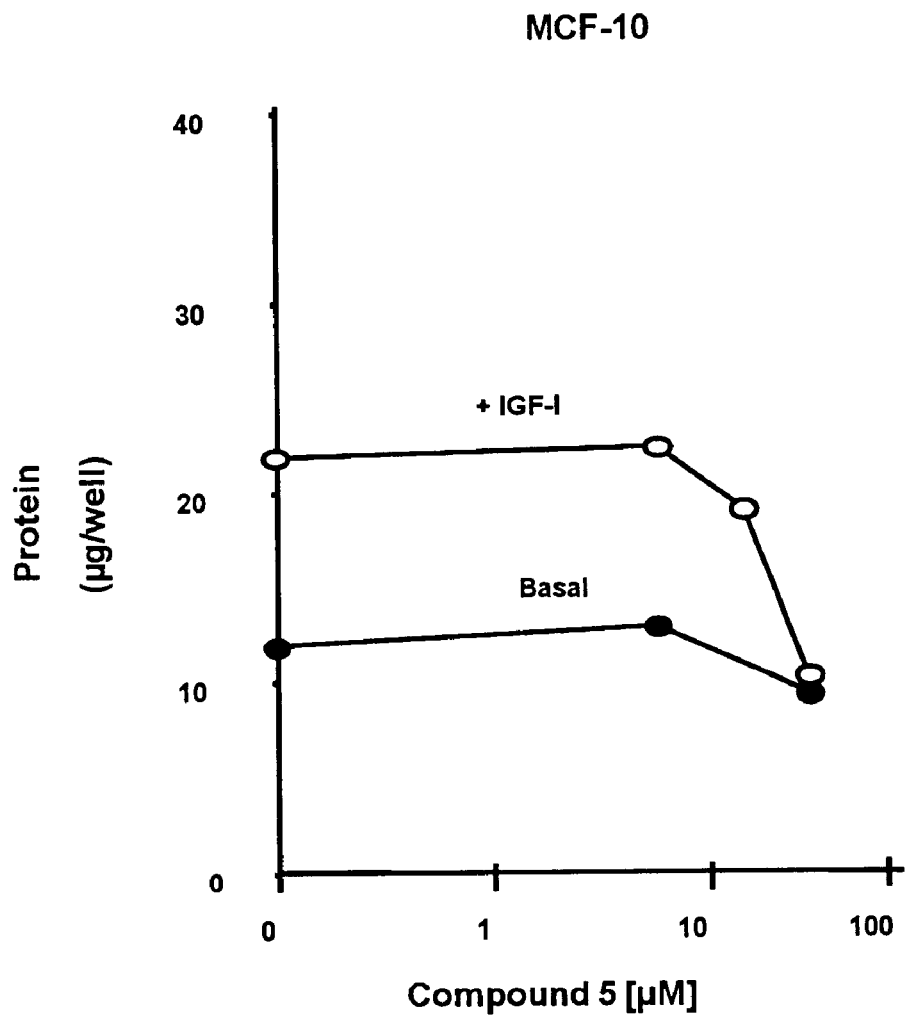
FIG. 1 shows the effect of N-(2-methoxy-3-chlorophenyl)-N'-(2-methyl-4-quinolinyl) urea (compound 5, see Example 2) on IGF-1 stimulated growth in MCF-10 cells (FIG. 1a), and MCF-7 cells (FIG. 1b).

The invention relates to the use of heteroaryl-aryl urea compounds which have been found to be antagonists of the IGF-1 receptor. The generic formula of the heteroaryl-aryl urea compounds useful in the present invention is as follows:

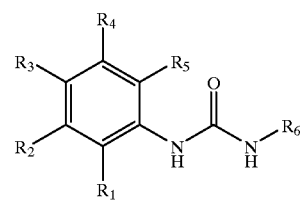

Formula I wherein $R_1$–$R_5$ are, independently, hydrogen, lower alkyl, substituted lower alkyl, hydroxyl, lower alkoxy, lower acyl, lower alkenyl, lower alkylthio, lower alkynyl, halo, $C(O)NR_7R_8$, $COOR_9$, $NR_{10}R_{11}$, a heterocyclic residue, aryl, aralkyl, cyano or nitro, any two adjacent substituents $R_1$–$R_5$ optionally together forming a lower alkylenedioxy, $R_6$ is a heterocyclic residue, $R_7$, $R_8$, $R_9$ are, independently, hydrogen, lower alkyl, substituted lower alkyl, aryl, aralkyl, or a heterocyclic residue, $R_{10}$, $R_{11}$ are, independently, hydrogen, lower alkyl, substituted lower alkyl, aryl, lower acyl, aralkyl, or a heterocyclic residue, and $R_7$ and $R_8$ or $R_{10}$ and $R_{11}$ together with the nitrogen may form a heterocyclic residue.

As used herein, "lower alkyl" refers to $C_{1-10}$ alkyl groups which may be linear, branched, or cyclic. The term lower alkyl includes such moieties as methyl, ethyl, propyl, butyl, pentyl, hexyl, heptyl, octyl, nonyl, decyl, cyclopentyl, or cyclohexyl, and those moieties which are positional isomers of these moieties. $C_{1-6}$ lower alkyls are preferred.

"Substituted lower alkyl" refers to a lower alkyl group substituted with hydroxyl, aryl, lower alkoxy, lower acyl, amido, amino, nitro, cyano, halo and the like.

"Lower alkenyl" refers to any branched or unbranched unsaturated $C_{2-10}$ group having the number of carbon atoms specified, or up to 22 carbon atoms if no limitation on the number of carbon atoms is specified; and having 1 or more double bonds in the group. Lower alkenyl is exemplified by ethenyl, propenyl, butenyl, pentenyl, hexenyl, heptenyl, octenyl, noneneyl, and decenyl, in their various isomeric forms, where the unsaturated bond(s) can be located anywhere in the group.

"Lower alkynyl" refers to hydrocarbon radicals of the scope of lower alkenyl, but having 1 or more triple bonds in the group.

"Lower alkoxy" refers to a lower alkyloxy group.

"Aryl" refers to an aromatic moiety of $C_{6-20}$, preferably $C_{6-16}$, having a single ring (e.g., phenyl), or two or more condensed rings, preferably 2 to 3 condensed rings (e.g., naphthyl), or two or more aromatic rings, preferably 2 to 3 aromatic rings, which are linked by a single bond (e.g., biphenyl). The aryl moiety may optionally be mono, di, or tri substituted, independently, with lower branched or straight chain alkyl, lower cycloalkyl with 3 to 12 carbon atoms, lower branched or straight chain alkoxy, lower cycloalkoxy with 3 to 12 carbon atoms, fluoro, chloro, bromo, trifluoromethyl, cyano, nitro and/or difluoromethoxy.

The term "heterocyclic residue", as used herein, includes heteroaryl and partially or completely hydrogenated heteroaryl. Typically, the heterocyclic residue contains from 2 to 12 carbon atoms with at least 1, preferably 1 to 3 heteroatoms, in its ring system. Typically, the heterocyclic residue will be a single heteroaryl ring, such as pyridyl, furyl, thienyl or isoxazolyl, or a ring system with two rings, preferably two condensed rings, such as quinolinyl, isoquinolinyl, benzofuranyl, benzofurazanyl, indolinyl, or a partially or completely hydrogenated heterocylic residue derived from these heteroaryl residues. Alternative heterocyclic residues include indazolyl and tetrahydroquinolinyl. The heterocyclic residue may have from one to four (preferably, not more than three) substituents, such as lower alkyl, substituted lower alkyl, lower alkoxy, halo, lower acyl, cyano, lower alkenyl, lower alkylthio, lower alkynyl, $C(O)NR_7R_8$, $COOR_9$, $NR_{10}R_{11}$, a heterocyclic residue, aryl, aralkyl, nitro or the like. Any two adjacent substituents on the heterocyclic residue may optionally together form a lower alkylenedioxy.

"Aralkyl" refers to a $C_{7-11}$ group containing a lower alkyl group to which is attached an aryl group such as benzyl, phenethyl, 3-phenylpropyl, or the like.

Certain compounds of formula I may contain one or more asymmetric centers resulting in multiple stereoisomers. In such case, all stereoisomers also fall within this scope.

In one embodiment of the invention, $R_6$ is selected from the group consisting of a quinolinyl, isoquinolinyl, thiazolyl, and acridinyl. In a preferred embodiment, $R_6$ is a quinolinyl or thiazolyl.

In one embodiment, R6 is a heterocyclic residue that has from one to three substituents selected from the group consisting of lower alkyl, substituted lower alkyl, hydroxyl, lower alkoxy, lower acyl, lower alkenyl, lower alkylthio, lower alkynyl, halo, $C(O)NR_7R_8$, $COOR_9$, $NR_{10}R_{11}$, a heterocyclic residue, aryl, aralkyl, cyano or nitro.

In one embodiment of the invention, at least two of the substituents $R_1-R_5$ are hydrogen. In a preferred embodiment, at least three of the substituents $R_1-R_5$ are hydrogen. In a further preferred embodiment, three to four of the substituents $R_1-R_5$ are hydrogen. In a further preferred embodiment, $R_6$ is 2-methyl-4-quinolinyl, $R_1$ is methoxy, $R_2$ is chloro, and $R_3-R_5$ are hydrogen.

In one embodiment of the invention, the heteroaryl-aryl urea is selected from the group consisting of N-(3-chloro-4-methylphenyl)-N'-(2-methyl-4-quinolinyl) urea, N-(2-methoxyphenyl)-N'-(2-methyl-4-quinolinyl) urea, N-(3-chlorophenyl)-N'-(2-methyl-4-quinolinyl) urea, N-(3,5-dichlorophenyl)-N'-(2-methyl-4-quinolinyl) urea, N-(2-methoxy-3-chlorophenyl)-N'-(2-methyl-4-quinolinyl) urea, N-(4-ethylphenyl)-N'-(2-methyl-4-quinolinyl) urea, N-(2-methoxy-5-chlorophenyl)-N'-(2-methyl-4-quinolinyl) urea, N-(3-chloro-4-methylphenyl)-N'-(3-quinolinyl) urea, N-(4-ethylphenyl)-N'-(8-quinolinyl) urea, N-(3-chlorophenyl)-N'-(3-quinolinyl) urea, N-(2-methoxy-3-chlorophenyl)-N'-(1,3-thiazol-2-yl) urea, N-(3-chloro-4-methylphenyl)-N'-(1,3-thiazol-2-yl) urea, N-(2-methoxyphenyl)-N'-(1,3-thiazol-2-yl) urea, and N-(3,5-dichlorophenyl)-N'-(1,3-thiazol-2-yl) urea.

Pharmaceutically acceptable salts and anions of the compounds of formula I are suitable for use in the methods of the present invention. A "pharmaceutically acceptable salt" may be any salt derived from an inorganic or organic acid. The term "pharmaceutically acceptable anion" refers to the anion of such acid addition salts. The salt and/or the anion are chosen not to be biologically or otherwise undesirable.

Typically the parent compound is treated with an excess of an alkaline reagent, such as hydroxide, carbonate or alkoxide, containing the appropriate cation. Cations such as $Na^+$, $K^+$, $Ca^{2+}$ and $NH_4^+$ are examples of cations present in pharmaceutically acceptable salts. Salts may also be prepared using organic bases, such as diethanolamine, ehtanolamine, triethanolamine, diethanolamine, N-methylglucamine, ethanolamine, and triethanolamine. If the compounds of formula I contain a basic group, an acid addition salt may be prepared. Acid addition salts of the compounds are prepared in a standard manner in a suitable solvent from the parent compound and an excess of acid, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p toluene-sulfonic acid, hexanoic acid, heptanoic acid, cyclopentanepropionic acid, lactic acid, o-(4-hydroxy-benzoyl)benzoic acid, 1,2-ethanedisulfonic acid, 2-hydroxyethanesulfonic acid, benzenesulfonic acid, p-chlorobenzenesulfonic acid, 2-naphthalenesulfonic acid, camphorsulfonic acid, 4-methyl-bicyclo[2.2.2.]oct-2-ene-1-carboxylic acid, glucoheptonic acid, 4,4'-methylenebis(3-hydroxy-2-naphthoic)acid, 3-phenylpropionic acid, trimethyl-acetic acid, t-butylacetic acid, laurylsulfuric acid, glucuronic acid, glutamic acid, 3-hydroxy-2-naphthoic acid, stearic acid, muconic acid and the like. Certain of the compounds form inner salts or zwitterions, which may also be acceptable.

The ability of heteroaryl-aryl ureas of formula I to act as antagonists of IFG-1R is demonstrated in the specific examples listed below (Examples 3–5). In Example 3, data are presented which show that various different heteroaryl-aryl ureas of formula I possess the ability to inhibit phosphorylation of a substrate peptide by the cytoplasmic kinase domain of IGF-1R. In Example 4 and FIG. 1, a heteroaryl-aryl urea compound of formula I, N-(2-methoxy-3-chlorophenyl)[(2-methyl(4-quinolinyl))amino] carboxamide, is shown to inhibit IGF-1 stimulated cell growth. Similarly, Example 5 and FIG. 2 show that the same heteroaryl-aryl urea compound of formula I can inhibit IGF-1 stimulated cell proliferation. The IFG-1R antagonist activity of the heteroaryl-aryl urea compounds of formula I makes them suitable for use in the methods of the present invention.

In one embodiment of the invention, a method is provided for inhibiting the activity of the insulin-like growth factor-1 receptor in a mammalian cell. This method comprises administering an effective compound of formula I to the mammalian cell.

In an alternative embodiment of the invention, a method is provided for inhibiting the growth of a mammalian cell, and preferably a cell which is in a mammal. This method involves administering a compound of formula I to the cell in an amount sufficient to inhibit growth of the cell. If the targeted mammalian cell resides within a mammal, then the administration of the compound of formula I occurs without unacceptable toxic effects on the host mammal.

In a preferred embodiment, the cell is a tumor cell. The targeted tumor may optionally be in the brain, lung, liver, spleen, kidney, bladder, lymph node, small intestine, pancreas, colon, stomach, breast, endometrium, prostate, testicle, vulva, cervix, ovary, skin, head and neck, esophagus, or bone marrow. In a preferred embodiment, the cell is a tumor cell of the prostate or breast.

The heteroaryl-aryl ureas of formula I may also be used to promote apoptosis in a mammalian cell or to inhibit the escape of a cell from apoptosis. In such uses, a compound of formula I is administered to the cell in a sufficient quantity to achieve the desired effect.

The IFG-1R antagonist activity of the heteroaryl-aryl urea compounds of formula I also makes them suitable for use in the treatment of any IGF-1R-related disorders. In a preferred embodiment the heteroaryl-aryl urea compounds are used to treat cancer. The treatment of cancer includes, but is not limited to, the following effects: killing tumor cells, inhibiting tumor growth, inhibiting metastasis, decreasing tumor sized, reversing or reducing the malignant phenotype of tumor cells, and inducing an immune response directed towards tumor cells, or combinations thereof. The present invention provides for a method for treating cancer in a mammal comprises administering to the mammal a therapeutically effective amount of a compound of formula I. In a particularly preferred embodiment, the mammal is a human.

The cancer which is treated may optionally be a cancer selected from the group consisting of cancers of the brain, lung, liver, spleen, kidney, bladder, lymph node, small intestine, pancreas, colon, stomach, breast, endometrium, prostate, testicle, vulva, cervix, ovary, skin, head and neck, esophagus, bone marrow, or blood. In a preferred method, cancer of the prostate or breast is treated. Although in some cases it may be desirable to treat cancer in a mammal systemically, in most cases it will be preferable to target a cell which is either a tumor cell, a cell within a tumor, or a cell near a tumor.

The method of treating cancer in a mammal may optionally further comprise treating the mammal with an additional form of therapy for cancer. This additional form of therapy for cancer is preferably selected from an established form of therapy well-known to one of ordinary skill in the art. The additional form of therapy may include, but is not limited to, chemotherapy (including multi-drug resistance therapy), external beam radiation therapy, brachytherapy, gene therapy, and surgery.

To treat cancer, a compound of formula I may be combined with compositions comprising other agents effective in the treatment of cancer. These compositions would be provided in a combined amount effective to kill or inhibit proliferation of the cell. This process may involve introducing the heteroaryl-aryl urea and the additional agent(s) or factor(s) into the cell at the same time. This may be achieved by contacting the cell with a single composition or pharmaceutical formulation that includes both agents, or by exposing the cell to two distinct compositions or formulations, at the same time, wherein one composition includes the heteroaryl-aryl urea and the other includes the agent.

Alternatively, the heteroaryl-aryl urea treatment may precede or follow the other agent treatment by intervals ranging from minutes to weeks. In embodiments where the additional agent and the heteroaryl-aryl urea are applied separately to the mammalian cell, one would genely ensure that a significant period of time did not expire between the time of each delivery, such that the second agent and the heteroaryl-aryl urea would still be able to exert an advantageously combined effect on the cell. In such instances, it is contemplated that one would contact the cell with both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations. In summary, the compounds of the invention may be used for simultaneous, separate, or sequential use in the therapy of cancer, in combination with other forms of cancer treatment.

It also is conceivable that more than one administration of the heteroaryl-aryl urea or the other agent will be desired. Various combinations may be employed, where the heteroaryl-aryl urea of formula I is "A" and the other agent is "B", as exemplified below:

A/B/A B/A/B B/B/A A/A/B B/A/A A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Other combinations are contemplated. Again, to achieve cell killing, both agents are delivered to a cell in a combined amount effective to kill the cell.

Agents or factors suitable for use in a combined therapy include any chemical compound or treatment method that induces DNA damage when applied to a cell. Such agents and factors include radiation and waves that induce DNA damage such as, γ irradiation, X-rays, UV-irradiation, microwaves, electronic emissions, and the like.

In one embodiment of the invention, the radiation therapy which is combined with the administration of a heteroaryl-aryl urea composition constitutes external beam radiation. The external beam radiation treatment typically delivers high-energy radiation, such as high-energy x-ray beams. Alternatively, internal radiation, or brachytherapy, may be used in combination with the heteroaryl-aryl urea therapy. Methods of delivering brachytherapy include intracavitary or interstitial placement of radiation sources, instillation of colloidal solutions, and parenteral or oral administration. Sealed sources are encapsulated in a metal, wire, tube, needle, or the like. Unsealed radioactive sources are prepared in a suspension or solution.

A variety of chemical compounds, also described as "chemotherapeutic agents," function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-.based or actual compounds, such as the use of X-rays with cisplatin or the use of cisplatin with etoposide.

For example, in treating cancer according to the invention, one would contact the tumor cells with an agent in addition to the heteroaryl-aryl urea of formula I. This treatment may be in combination with irradiation of the tumor with radiation such as X-rays, UV-light, gamma-rays or even microwaves. Alternatively, the tumor cells may be contacted with the agent by administering to the subject a therapeutically effective amount of a pharmaceutical composition comprising a compound such as, adriamycin, 5-fluorouracil, etoposide, camptothecin, actinomycin-D, mitomycin C, or more preferably, cisplatin. The agent may be prepared and used as a combined therapeutic composition, or kit, by combining it with a heteroaryl-aryl urea of formula I, as described above.

Agents that directly cross-link nucleic acids, specifically DNA, are envisaged to facilitate DNA damage leading to a synergistic, antineoplastic combination with the expression constructs of the present invention. Agents such as cisplatin, and other DNA alkylating agents may be used. Cisplatin is not absorbed orally and must therefore be delivered via injection intravenously, subcutaneously, intratumorally or intraperitoneally. Agents that damage DNA also include compounds that interfere with DNA replication, mitosis and chromosomal segregation. Such chemotherapeutic compounds include adriamycin (also known as doxorubicin), etoposide, podophyllotoxin, and the like. Widely used in a clinical setting for the treatment of neoplasms, these compounds are administered through bolus injections intravenously at doses ranging from 25–75 mg/m$^2$ at 21 day intervals for adriamycin, to 100 mg/m$^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 450–1000 mg/m$^2$/day being commonly used.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The regional delivery of the heteroaryl-aryl urea compounds of formula I to patients with cancer is a preferred method for delivering a therapeutically effective gene to counteract the clinical disease being treated. Similarly, the chemo- or radiotherapy may be directed to a particular, affected region of the subject's body. Alternatively, systemic delivery of the heteroaryl-aryl urea compound of formula I and/or the agent may be appropriate in certain circumstances, for example, where extensive metastasis has occurred.

In an alternative embodiment of the invention, a therapeutically effective, substantially non-toxic amount of a compound of formula I is administered to an abnormal growth in a method for treating the abnormal growth in a mammal, preferably a human. In still another embodiment, a therapeutically effective amount and substantially non-toxic amount of a heteroaryl-aryl urea of formula I is administered to a tissue in a mammal, preferably a human, in a method for treating an IGF-1R-related condition in a mammal. Any IGF-1R-related disease condition may be treated in this manner as long as activity by the insulin-like growth factor-1 receptor plays a role in the disease condition and antagonism of the receptor leads to the amelioration of at least one undesirable symptom or indication of the disease condition.

The compounds of formula I are thus used to antagonize the IGF-1R in patients which require such treatment. The method of treatment comprises the administration parenterally, and orally, of an effective quantity of the chosen compound, preferably dispersed in a pharmaceutical carrier appropriate for the intended application. Generally this will entail preparing a pharmaceutical compositions that is essentially free of pyrogens, as well as any other impurities that could be harmful to humans or animals. One also will generally desire to employ appropriate salts and buffers to render the complex stable and allow for complex uptake by target cells.

A "therapeutically effective amount" of compound I is defined herein as the amount required to achieve the desired positive effect with respect to the particular IGF-1R-related disease condition being treated whether it be cancer or another disease condition. The effective amount will be determined in part based on the intended goal, for example, (i) inhibition of tumor cell proliferation versus (ii) elimination or killing of tumor cells.

Dosage units of the active ingredient are generally selected from the range of 0.01 to 1000 mg/kg, but will be readily determined by one skilled in the art depending upon the route of administration, age and condition of the patient. In one embodiment, the dosage unit is selected from the range of 1 to 1000 mg/kg. These dosage units may be administered one to ten times daily for acute or chronic disease. No unacceptable toxicological effects are expected when compounds of the invention are administered in accordance with the present invention.

Pharmaceutical compositions of the compounds of formula I, or derivatives thereof, may be formulated as solutions, crystalline, amorphous or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration. It may be desirable to add excipients such as polyvinylpyrrolidinone, gelatin, hydroxycellulose, acacia, polyethylene glycol, mannitol, sodium chloride or sodium citrate. Alternatively, these compounds may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, soybean oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glycerol monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of syrup, elixir, emulsion or an aqueous or non-aqueous suspension. Such a liquid formulation may be administered directly p.o. or filled into a soft gelatin capsule.

The invention compounds may be administered by any route suitable to the subject being treated and the nature of the subject's condition. Alternative routes of administration include administration by injection, including intravenous, intraperitoneal, intramuscular, and subcutaneous injection, by transmucosal or transdermal delivery, through topical applications, nasal spray, suppository and the like or may be administered orally. For application against tumors, direct intratumoral injection, injection of a resected tumor bed, regional (e.g. lymphatic) or systemic administration is contemplated. It also may be desired to perform continuous perfusion over hours or days via a catheter to a disease site like a tumor or tumor site. Suitable formulations for each of these methods of administration may be found, for example, in *Remington's Pharmaceutical Sciences*, latest edition, Mack Publishing Company, Easton, Pa.

EXAMPLES

The Examples that follow serve to illustrate this invention. The Examples are intended to in no way limit the scope of this invention, but are provided to show how to make and use the compounds of this invention.

The compounds of this invention are known compounds which can be prepared by conventional methods of organic chemistry. In some cases, protective groups may be introduced and finally removed. Suitable protective groups for amino, hydroxyl, carboxyl groups are described in Greene et al., *Protective Groups in Organic Synthesis*, Second Edition, John Wiley and Sons, New York, 1991. A number of different procedures for preparing isocyanates can be found in Larock, *Comprehensive Organic Transformations*, VCH Publishers, New York, 1989.

Since heteroarylaryl ureas are common compounds, methods of preparing heteroaryl-aryl ureas are well known to one of ordinary skill in the art. For instance, examples of preparations of heteroaryl-aryl ureas useful in the present invention can be found in the PCT Publication WO 94/18170, herein incorporated by reference. Known methods of preparing these types of compounds can be found in Chapter 6 in *Organic Functional Group Preparations* Vol 12-II, Sandler, Karo ed., Academic Press, New York, 1971, Buckman et al., *Tet. Lett.* 1996, 37:4439, and Stewart et al., *J. Med. Chem.*, 1970, 13:762, all of which are herein incorporated by reference.

Example 1

Preparation of N-(3-chloro-4-methylphenyl)-N'-(2-methyl-4-quinolinyl) urea, Compound 1

The reaction scheme for the preparation of N-(3-chloro-4-methylphenyl)[(2-methyl(4-quinolinyl))amino]carboxamide, 1 is shown below:

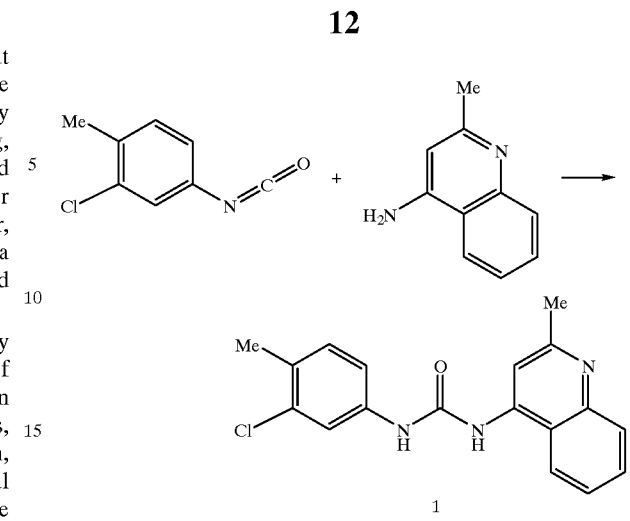

To a solution of 4-quinolinylamine (1 mmol) in $CH_2Cl_2$ at room temperature was added slowly 3-Chloro-4-methylbenzenisocyanate (1.1 mmol). The reaction was allowed to stir for 2 h, and precipitation occurred. The reaction mixture was filtered and a white solid collected. This was recrystallized from hexane/EtOAc to afford white crystals.

Example 2

Preparation of Additional Heteroaryl-aryl Ureas

The compounds shown in Table 1, below, were prepared using procedures similar to those in Example 1, above.

TABLE 1

| Compound | R1 | R2 | R3 | R4 | R5 | R6 |
|---|---|---|---|---|---|---|
| 1 | H | Cl | Me | H | H | 2-methyl-4-quinolinyl |
| 2 | OMe | H | H | H | H | 2-methyl-4-quinolinyl |
| 3 | H | Cl | H | H | H | 2-methyl-4-quinolinyl |
| 4 | H | Cl | H | Cl | H | 2-methyl-4-quinolinyl |
| 5 | OMe | Cl | H | H | H | 2-methyl-4-quinolinyl |
| 6 | H | H | Et | H | H | 2-methyl-4-quinolinyl |
| 7 | OMe | H | H | Cl | H | 2-methyl-4-quinolinyl |
| 8 | H | Cl | Me | H | H | 3-quinolinyl |
| 9 | H | H | Et | H | H | 8-quinolinyl |
| 10 | H | Cl | H | H | H | 3-quinolinyl |
| 11 | OMe | Cl | H | H | H | 1,3-thiazol-2-yl |
| 12 | H | Cl | Me | H | H | 1,3-thiazol-2-yl |
| 13 | OMe | H | H | H | H | 1,3-thiazol-2-yl |
| 14 | H | Cl | H | Cl | H | 1,3-thiazol-2-yl |

Example 3

IGF-1R Substrate Assay

Nunc Maxisorp plates were coated with 100 μL 10 μg/mL-streptavidin at 4° C. for 2 hr at 25–37° C. The plates were washed in 20 mM Tris pH7.6, 150 mM NaCl, 0.05% Tween 20, 0.8 mM $Na_3VO_4$, and 0.04% Biocide between all steps of the assay. The plates were blocked in 200 μL 50 mM Hepes/150 mM NaCl/0.1% Triton-X 100 overnight at 4° C. or for 2 hr at 25–37° C.

Aliquots of the IGF-1R-cytoplasmic kinase domain (IGF-1R-CKD; amino acids 959–1367 of IGF-1R) were purified and stored at −80° C. until use. KS2 (GPWLEEEEEAYGWMDF; SEQ ID NO:1), gastrin (1–17) that is a substrate for many tyrosine kinases including the insulin receptor, was synthesized as a biotin conjugate (KS2-biotin) (Baldwin et al., Nature, 301:435–37 (1983)). The assay mixture consisted of 0.2 µg/mL IGF-1R-CKD (concentration adjusted for optimal response), 300–900 nM KS2-biotin (depending on optimal response), 2 mM $MnCl_2$, 5 mM $MgCl_2$ (4–10 mM $MnCl_2$ can be substituted), compounds to be tested (50 µM) or their vehicle, and 50 µM ATP. The start of phosphorylation begins with the addition of ATP. Incubation was continued for 10–30 minutes, at which time, the reaction was stopped through the quenching the metals with 20 mM EDTA (final concentration).

The reaction was diluted 1:10 in buffer A (2 mM HEPES pH 7.6, 0.05% Triton X-100, 0.05% bovine serum albumin (BSA)) and 100 µL was captured onto washed, coated and blocked, streptavidin Nunc Maxisorp plate, overnight at 4° C. or 2 hr at 37° C. Anti-phosphotyrosine antibody (12.5 ng/well) conjugated to horseradish peroxidase (RC20:HRPO by Transduction Laboratories) was diluted into 0.5X Buffer B (25 mM Hepes pH7.6, 75 mM NaCl, 0.025% Tween 20, 2 mM $Na_3VO_4$+1% BSA) and incubated for 1.5 to 2 hr at 25° C. The phosphorylated substrate was measured by developing the plate with 100 µL 3', 3', 5,5' tetramethylbenzidine (TMB), and quantified using a plate reader.

The phosphorylation of KS2 by IGF-1R-CKD was found to be inhibited by heteroaryl-aryl urea compounds of Examples 1 and 2. The results are shown below in Table 2.

TABLE 2

Inhibition of KS2 phosphorylation by the IGF-1R CKD in the presence of heteroaryl-aryl ureas.

| Compound | % Inhibition |
|---|---|
| 5 | 21 |
| 7 | 23 |
| 8 | 65 |
| 9 | 33 |
| 10 | 26 |
| 11 | 21 |
| 12 | 21 |
| 13 | 20 |
| 14 | 17 |

Example 4

Cell Growth Inhibition Study by Protein Assay 100,000 cells (MCF-7) were plated into 24 well dishes, and grown in complete Dulbecco's modified Eagle's medium (DMEM) supplemented with 10% fetal calf serum (FCS) for 24 h. Cells were washed twice in serum-free DMEM, then 0.5 ml DMEM supplemented with $0^5$% FCS and 1 nM IGF-1 was added with or without a heteroaryl-aryl compound, compound 5, and in the presence or absence of 1 nM hormone (IGF-1 or insulin, respectively). After 48 h at 37° C., cells were washed twice with phosphate buffered saline (PBS) then solubilized in 0.03% sodium dodecyl sulfate (SDS). Protein was determined using the BCA Protein Assay reagent from Pierce Chemical with BSA serving as a standard.

MFC-10 cells were plated as above in DMEM/Ham's F12 medium (DMEM/F12) supplemented with 5% horse serum, 8 ng/ml epidermal growth factor (EGF), 0.5 µg/ml hydrocortisone, 0.1 µg/mL cholera toxin. After 24 hr, cells were washed twice in serum free DMEM/F12, then 0.5 ml DMEM/12 with 0.5% horse serum added with or without test compound, and in the absence of 1 nM IGF-I.

Figure 1B:
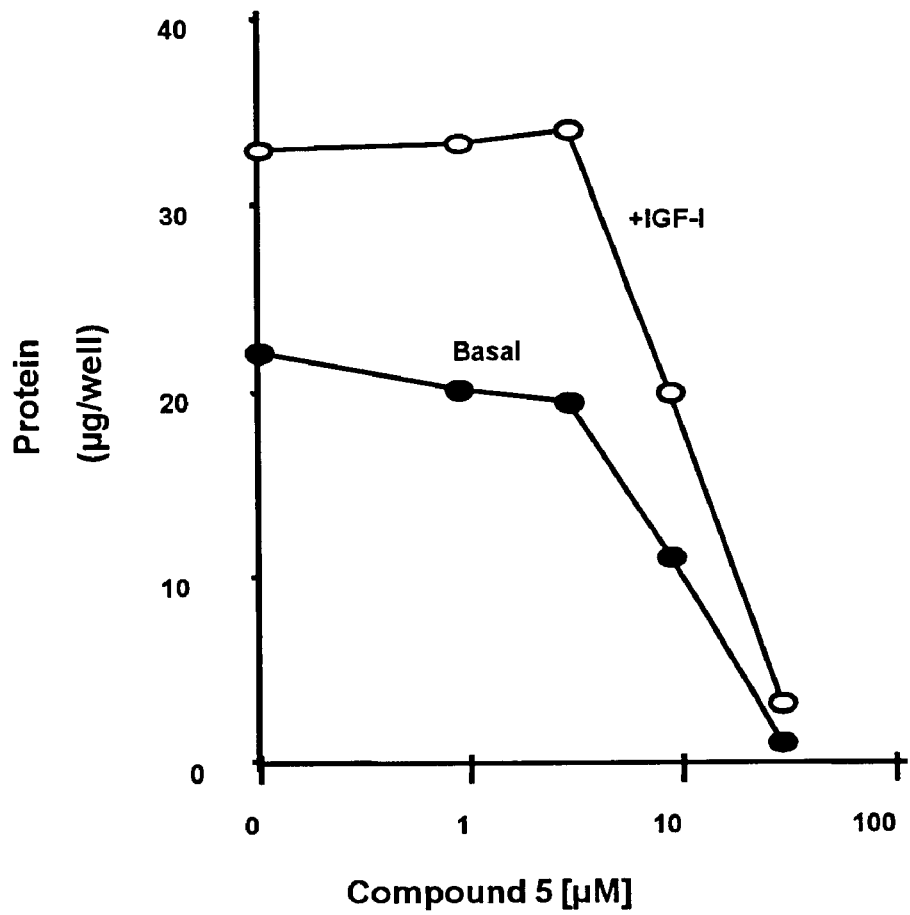
Figure 2:
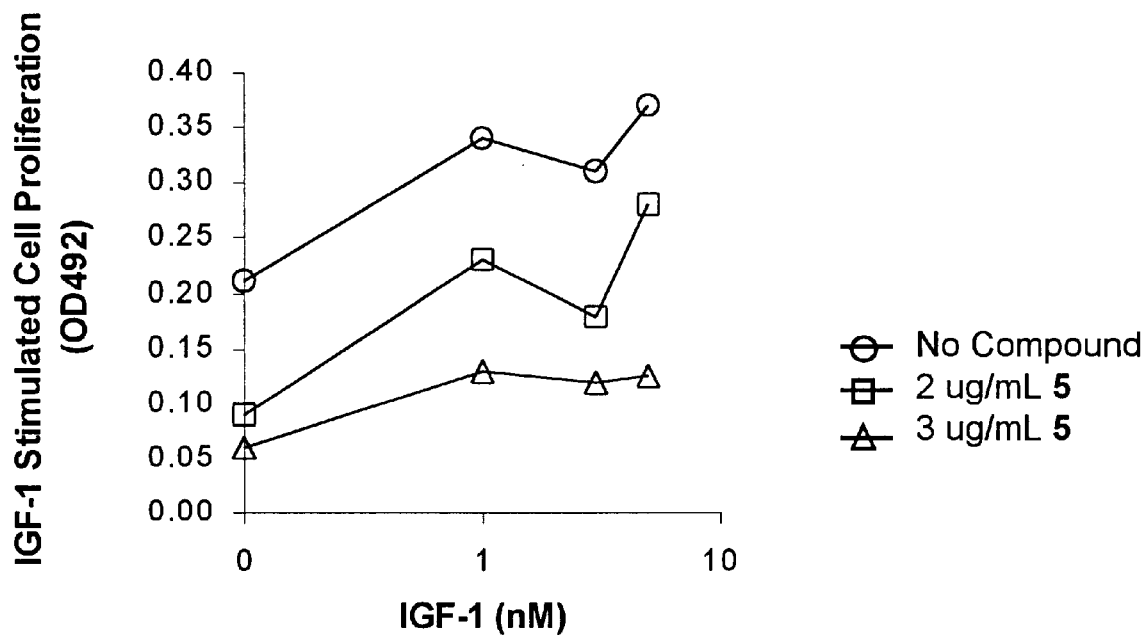
FIG. 2 shows the effect of N-(2-methoxy-3-chlorophenyl)-N'-(2-methyl-4-quinolinyl) urea (compound 5, see Example 2) on IGF-1 stimulated cell proliferation.

The results of the protein assay are shown in FIG. 1a and 1b. Addition of the heteroaryl-aryl urea test compound, compound 5, was found to inhibit IGF-1 stimulated cell growth.

Example 5

Cell Proliferation Assay 5000 cells (MCF-7 or MCF-10) were plated into 96 well plates and grown for 24 h as in Example 4, above. Cells were washed in serum free DMEM, then 100 µl media and 1 nM IGF-1 were added to wells in the presence of or absence of compound 5 (see Example 2) and hormone. After 48 h, viability was determined by CellTiter 96™ (Promega). This kit is a chromogenic bioassay procedure for the measurement of cell proliferation. Briefly, 20 µl (3-[4,5, dimethylthiazol-2-yl]-5-[3-carboxymethoxyphenyl]-2-[4-sulfophenyl]-2H-tetrazolium, inner salt (MTS) was added to each well and incubation was continued for 3–4 h. Viable cells reduced the MTS to formazan, which was then measured at 492 nm using an ELISA plate reader. Cell proliferation was calculated based on the increase in the number of viable cells.

The results of the cell proliferation assay are shown in FIG. 2. The data show that the addition of the heteroaryl-aryl urea test compound, compound 5, led to a decrease in IGF-1R stimulated cell proliferation.

Example 6

Oral Pharmaceutical Composition Preparation— Solid Dosage Formulation

A pharmaceutical composition for oral administration may be prepared by combining the following:

| | % w/w |
|---|---|
| Compound of formula I | 10% |
| Magnesium stearate | 0.5% |
| Starch | 2.0% |
| HPM cellulose | 1.0% |
| Microcrystalline cellulose | 86.5% |

The mixture may be compressed to tablets, or filled into hard gelatin capsules.

The tablet may be coated by applying a suspension of film former (e.g. HPM cellulose), pigment (e.g. titanium dioxide) and plasticiser (e.g. diethyl phthalate) and drying the film by evaporation of the solvent. The film coat can comprise 2.0% to 6.0% of the tablet weight, preferably about 3.0%.

Example 7

Oral Pharmaceutical Composition Preparation— Capsule

A pharmaceutical composition of a compound of formula I suitable for oral administration may also be prepared by combining the following:

| | % w/w |
|---|---|
| Compound of formula I | 20% |
| Polyethylene glycol | 80% |

The medicinal compound is dispersed or dissolved in the liquid carrier, with a thickening agent added, if required. The formulation is then enclosed in a soft gelatin capsule by suitable technology.

Example 8

Pharmaceutical Composition for Parenteral Administration

A pharmaceutical composition for parenteral administration may be prepared by combining the following:

| | Preferred Level |
|---|---|
| Compound of formula I | 1.0% |
| Saline | 99.0% |

The solution is sterilized and sealed in sterile containers.

All documents cited in the above specification are herein incorporated by reference. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What we claim is:

1. A method for inhibiting the activity of the insulin-like growth factor-1 receptor in a mammalian cell, comprising: administering to said mammalian cell an effective amount of a compound of the formula

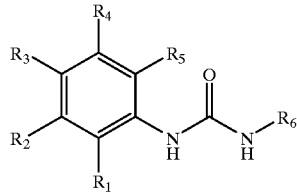

or a pharmaceutically acceptable salt thereof, wherein
$R_1$–$R_5$ are, independently, hydrogen, lower alkyl, substituted lower alkyl, hydroxyl, lower alkoxy, lower acyl, lower alkenyl, lower alkynyl, halo, $C(O)NR_7R_8$, $COOR_9$, $NR_{10}R_{11}$, aryl, aralkyl, cyano or nitro,
$R_6$ is quinolinyl or thiazolyl,
$R_7$, $R_8$, $R_9$ are, independently, hydrogen, lower alkyl, substituted lower alkyl, aryl, or aralkyl, and
$R_{10}$, $R_{11}$, are, independently, hydrogen, lower alkyl, substituted lower alkyl, aryl, lower acyl, or aralkyl.

2. The method of claim 1, wherein three to four of the substituents $R_1$–$R_4$ are hydrogen.

3. The method of claim 2, wherein said compound is selected from the group consisting of N-(3-chloro-4-methylphenyl)-N'-(2-methyl-4-quinolinyl) urea,
N-(2-methoxyphenyl)-N'-(2-methyl-4-quinolinyl) urea,
N-(3-chlorophenyl)-N'-(2-methyl-4-quinolinyl) urea,
N-(3,5-dichlorophenyl)-N'-(2-methyl-4-quinolinyl) urea,
N-(2-methoxy-3-chlorophenyl)-N'-(2-methyl-4-quinolinyl) urea,
N-(4-ethylphenyl)-N'-(2-methyl-4-quinolinyl) urea,
N-(2-methoxy-5-chlorophenyl)-N'-(2-methyl-4-quinolinyl) urea,
N-(3-chloro-4-methylphenyl)-N'-(3-quinolinyl) urea,
N-(4-ethylphenyl)-N'-(8-quinolinyl) urea,
N-(3-chlorophenyl)-N'-(3-quinolinyl) urea,
N-(2-methoxy-3-chlorophenyl)-N'-(1,3-thiazol-2-yl) urea,
N-(3-chloro-4-methylphenyl)-N'-(1,3-thiazol-2-yl) urea,
N-(2-methoxyphenyl)-N'-(1,3-thiazol-2-yl) urea, and
N-(3,5-dichlorophenyl)-N'-(1,3-thiazol-2-yl) urea as a single stereoisomer or as a mixture thereof, or the pharmaceutically acceptable salts thereof.

4. A method for inhibiting the growth of a cell in a mammal, comprising:
administering to said cell a compound of the formula

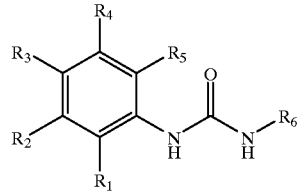

or a pharmaceutically acceptable salt thereof, wherein
$R_1$–$R_5$ are, independently, hydrogen, lower alkyl, substituted lower alkyl, hydroxyl, lower alkoxy, lower acyl, lower alkenyl, lower alkynyl, halo, $C(O)NR_7R_8$, $COOR_9$, $NR_{10}R_{11}$, aryl, aralkyl, cyano or nitro,
$R_6$ is quinolinyl or thiazolyl,
$R_7$, $R_8$, $R_9$ are independently, hydrogen, lower alkyl, substituted lower alkyl, aryl, or aralkyl, and
$R_{10}$, $R_{11}$, are, independently, hydrogen, lower alkyl, substituted lower alkyl, aryl, lower acyl, or aralkyl,
in an amount sufficient to inhibit the growth of said cell, without exhibiting unacceptable toxic effects on the mammalian host.

5. The method of claim 4, wherein three to four of the substituents $R_1$–$R_5$ are hydrogen.

6. The method of claim 5, wherein said compound is selected from the group consisting of N-(3-chloro-4-methylphenyl)-N'-(2-methyl-4-quinolinyl) urea,
N-(2-methoxyphenyl)-N'-(2-methyl-4-quinolinyl) urea,
N-(3-chlorophenyl)-N'-(2-methyl-4-quinolinyl) urea,
N-(3,5-dichlorophenyl)-N'-(2-methyl-4-quinolinyl) urea,
N-(2-methoxy-3-chlorophenyl)-N'-(2-methyl-4-quinolinyl) urea,
N-(4-ethylphenyl)-N'-(2-methyl-4-quinolinyl) urea,
N-(2-methoxy-5-chlorophenyl)-N'-(2-methyl-4-quinolinyl) urea,
N-(3-chloro-4-methylphenyl)-N'-(3-quinolinyl) urea, N-(4-ethylphenyl)-N'-(8-quinolinyl) urea,
N-(3-chlorophenyl)-N'-(3-quinolinyl) urea,
N-(2-methoxy-3-chlorophenyl)-N'-(1,3-thiazol-2-yl) urea,
N-(3-chloro-4-methylphenyl)-N'-(1,3-thiazol-2-yl) urea,
N-(2-methoxyphenyl)-N'-(1,3-thiazol-2-yl) urea, and
N-(3,5-dichlorophenyl)-N'-(1,3-thiazol-2-yl) urea as a single stereoisomer or as a mixture thereof, or the pharmaceutically acceptable salts thereof.

7. The method of claim 4, wherein said cell is a tumor cell.

8. A method for promoting apoptosis of a tumor cell, comprising:

administering to said tumor cell a compound of formula

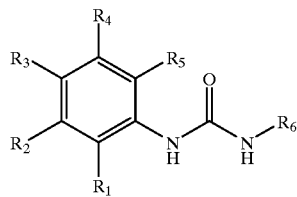

or a pharmaceutically acceptable salt thereof, wherein
$R_1$–$R_5$ are, independently, hydrogen, lower alkyl, substituted lower alkyl, hydroxyl, lower alkoxy, lower acyl, lower alkenyl, lower alkynyl, halo, C(O)NR$_7$R$_8$, COOR$_9$, NR$_{10}$R$_{11}$, aryl, aralkyl, cyano or nitro,
$R_6$ is quinolinyl or thiazolyl,
$R_7$, $R_8$, $R_9$ are independently, hydrogen, lower alkyl, substituted lower alkyl, aryl, or aralkyl, and
$R_{10}$, $R_{11}$, are, independently, hydrogen, lower alkyl, substituted lower alkyl, aryl, lower acyl, or aralkyl,
in an amount sufficient to promote apoptosis of said tumor cell.

9. The method of claim 8, wherein three to four of the substituents $R_1$–$R_5$ are hydrogen.

10. The method of claim 9, wherein said compound is selected from the group consisting of
N-(3-chloro-4-methylphenyl)-N'-(2-methyl-4-quinolinyl) urea,
N-(2-methoxyphenyl)-N'-(2-methyl-4-quinolinyl) urea,
N-(3-chlorophenyl)-N'-(2-methyl-4-quinolinyl) urea,
N-(3,5-dichlorophenyl)-N'-(2-methyl-4-quinolinyl) urea,
N-(2-methoxy-3-chlorophenyl)-N'-(2-methyl-4-quinolinyl) urea,
N-(4-ethylphenyl)-N'-(2-methyl-4-quinolinyl) urea,
N-(2-methoxy-5-chlorophenyl)-N'-(2-methyl-4-quinolinyl) urea,
N-(3-chloro-4-methylphenyl)-N'-(3-quinolinyl) urea,
N-(4-ethylphenyl)-N'-(8-quinolinyl) urea,
N-(3-chlorophenyl)-N'-(3-quinolinyl) urea,
N-(2-methoxy-3-chlorophenyl)-N'-(1,3-thiazol-2-yl) urea,
N-(3-chloro-4-methylphenyl)-N'-(1,3-thiazol-2-yl) urea,
N-(2-methoxyphenyl)-N'-(1,3-thiazol-2-yl) urea, and
N-(3,5-dichlorophenyl)-N'-(1,3-thiazol-2-yl) urea as a single stereoisomer or as a mixture thereof, or the pharmaceutically acceptable salts thereof.

11. A method for treating prostate or breast cancer in a mammal, comprising:

administering to said mammal a therapeutically effective, substantially non-toxic amount of a compound of the formula

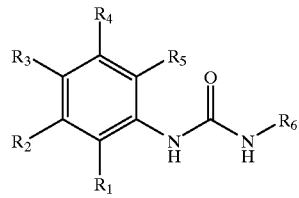

or a pharmaceutically acceptable salt thereof, wherein
$R_1$–$R_5$ are, independently, hydrogen, lower alkyl, substituted lower alkyl, hydroxyl, lower alkoxy, lower acyl, lower alkenyl, lower alkynyl, halo, C(O)NR$_7$R$_8$, COOR$_9$, NR$_{10}$R$_{11}$, aryl, aralkyl, cyano or nitro,
$R_6$ is quinolinyl or thiazolyl,
$R_7$, $R_8$, $R_9$ are independently, hydrogen, lower alkyl, substituted lower alkyl, aryl, or aralkyl, and
$R_{10}$, $R_{11}$, are, independently, hydrogen, lower alkyl, substituted lower alkyl, aryl, lower acyl, or aralkyl.

12. The method of claim 11, wherein three to four of the substituents $R_1$–$R_5$ are hydrogen.

13. The method of claim 12, wherein said compound is selected from the group consisting of
N-(3-chloro-4-methylphenyl)-N'-(2-methyl-4-quinolinyl) urea,
N-(2-methoxyphenyl)-N'-(2-methyl-4-quinolinyl) urea,
N-(3-chlorophenyl)-N'-(2-methyl-4-quinolinyl) urea,
N-(3,5-dichlorophenyl)-N'-(2-methyl-4-quinolinyl) urea,
N-(2-methoxy-3-chlorophenyl)-N'-(2-methyl-4-quinolinyl) urea,
N-(4-ethylphenyl)-N'-(2-methyl-4-quinolinyl) urea,
N-(2-iethoxy-5-chlorophenyl)-N'-(2-methyl-4-quinolinyl) urea,
N-(3-chloro-4-methylphenyl)-N'-(3-quinolinyt) urea,
N-(4-ethylphenyl)-N'-(8-quinolinyl) urea,
N-(3-chlorophenyl)-N'-(3-quinolinyl) urea,
N-(2-methoxy-3-chlorophenyl)-N'-(1,3-thiazol-2-yl) urea,
N-(3-chloro-4-methylphenyl)-N'-(1,3-thiazol-2-yl) urea,
N-(2-methoxyphenyl)-N'-(1,3-thiazol-2-yl) urea, and
N-(3,5-dichlorophenyl)-N'-(1,3-thiazol-2-yl) urea as a single stereoisomer or as a mixture thereof, or the pharmaceutically acceptable salts thereof.

14. The method of claim 11, wherein said mammal is a human.

15. The method of claim 11, further comprising treating said mammal with an additional form of therapy for cancer selected from the group consisting of chemotherapy, external beam radiation therapy, brachytherapy, gene therapy, and surgery.

16. The method of claim 11, wherein said cancer is prostate cancer or breast cancer.

17. A method for treating an abnormal growth in a mammal, comprising:

administering to said abnormal growth a therapeutically effective, substantially non-toxic amount of a compound of the formula

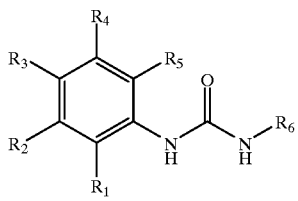

or a pharmaceutically acceptable salt thereof, wherein $R_1$–$R_5$ are, independently, hydrogen, lower alkyl, substituted lower alkyl, hydroxyl, lower alkoxy, lower acyl, lower alkenyl, lower alkynyl, halo, $C(O)NR_7R_8$, $COOR_9$, $NR_{10}R_{11}$, aryl, aralkyl, cyano or nitro, $R_6$ is quinolinyl or thiazolyl, $R_7$, $R_8$, $R_9$ are independently, hydrogen, lower alkyl, substituted lower alkyl, aryl, or aralkyl, and $R_{10}$, $R_{11}$, are, independently, hydrogen, lower alkyl, substituted lower alkyl, aryl, lower acyl, or aralkyl.

18. The method of claim 17, wherein three to four of the substituents $R_1$–$R_5$ are hydrogen.

19. The method of claim 18, wherein said compounds selected from the group consisting of N-(3-chloro-4-methylphenyl)-N'-(2-methyl-4-quinolinyl) urea, N-(2-methoxyphenyl)-N'-(2-methyl-4-quinolinyl) urea, N-(3-chlorophenyl)-N'-(2-methyl-4-quinolinyl) urea, N-(3,5-dichlorophenyl)-N'-(2-methyl-4-quinolinyl) urea, N-(2-methoxy-3-chlorophenyl)-N'-(2-methyl-4-quinolinyl) urea, N-(4-ethylphenyl)-N'-(2-methyl-4-quinolinyl) urea, N-(2-methoxy-5-chlorophenyl)-N'-(2-methyl-4-quinolinyl) urea, N-(3-chloro-4-methylphenyl)-N'-(3-quinolinyl) urea, N-(4-ethylphenyl)-N'-(8-quinolinyl) urea, N-(3-chlorophenyl)-N'-(3-quinolinyl) urea, N-(2-methoxy-3-chlorophenyl)-N'-(1,3-thiazol-2-yl) urea, N-(3-chloro-4-methylphenyl)-N'-(1,3-thiazol-2-yl) urea, N-(2-methoxyphenyl)-N'-(1,3-thiazol-2-yl) urea, and N-(3,5-dichlorophenyl)-N'-(1,3-thiazol-2-yl) urea as a single stereoisomer or as a mixture thereof, or the pharmaceutically acceptable salts thereof.

20. A method for treating an IGF-1R-related disease condition in a mammal by inhibiting the activity of IGF-1R in a tissue of the mammal, comprising:

administering to said tissue a therapeutically effective, substantially non-toxic amount of a compound of the formula

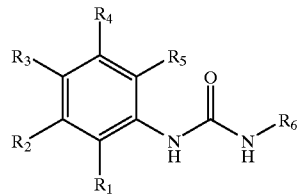

or a pharmaceutically acceptable salt thereof, wherein $R_1$–$R_5$ are, independently, hydrogen, lower alkyl, substituted lower alkyl, hydroxyl, lower alkoxy, lower acyl, lower alkenyl, lower alkynyl, halo, $C(O)NR_7R_8$, $COOR_9$, $NR_{10}R_{11}$, aryl, aralkyl, cyano or nitro, $R_6$ is quinolinyl or thiazolyl, $R_7$, $R_8$, $R_9$ are independently, hydrogen, lower alkyl, substituted lower alkyl, aryl, or aralkyl, and $R_{10}$, $R_{11}$, are, independently, hydrogen, lower alkyl, substituted lower alkyl, aryl, lower acyl, or aralkyl.

21. The method of claim 20, wherein three to four of the substituents $R_1$–$R_5$ are hydrogen.

22. The method of claim 21, wherein said compound is selected from the group consisting of N-(3-chloro-4-methylphenyl)-N'-(2-methyl-4-quinolinyl) urea, N-(2-methoxyphenyl)-N'-(2-methyl-4-quinolinyl) urea, N-(3-chloroplenyl)-N'-(2-methyl-4-quinolinyl) urea, N-(3,5-dichlorophenyl)-N'-(2-methyl-4-quinolinyl) urea, N-(2-methoxy-3-chlorophenyl)-N'-(2-methyl-4-quinolinyl) urea, N-(4-ethylphenyl)-N'-(2-methyl-4-quinol iny) urea, N-(2-methoxy-5-chlorophenyl)-N'-(2-methyl-4-quinolinyl) urea, N-(3-chloro-4-methylphenyl)-N'-(3-quinolinyl) urea, N-(4-ethylphenyl)-N'-(8-quinolinyl) urea, N-(3-chlorophenyl)-N'-(3-quinolinyl) urea, N-(2-methoxy-3-chlorophenyl)-N'-(1,3-thiazol-2-yl) urea, N-(3-chloro-4-methylphenyl)-N'-(1,3-thiazol-2-yl) urea, N-(2-methoxyphenyl)-N'-(1,3-thiazol-2-yl) urea, and N-(3,5-dichlorophenyl)-N'-(1,3-thiazol-2-yl) urea, as a single stereoisomer or as a mixture thereof, or the pharmaceutically acceptable salts thereof.

* * * * *

UNITED STATES PATENT AND TRADEMARK OFFICE
Certificate

Patent No. 6,337,338 B1                                                                                            Patented: January 8, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Michael R. Kozlowski, Palo Alto, CA (US); Robert T. Lum, Palo Alto, CA (US); Steven R. Schow, Redwood Shores, CA (US); Hugo O. Villar, Newark, CA (US); Michelle M. Wick, Woodside, CA (US); Ira D. Goldfine, Belvedere, CA (US); Betty A. Maddux, San Francisco, CA (US); and Jack F. Youngren, San Francisco, CA (US).

Signed and Sealed this Seventeenth Day of November 2009.

*JANET L. ANDES*
*Supervisory Patent Examiner*
*Art Unit 1625*